United States Patent
Pittman et al.

(10) Patent No.: US 7,810,497 B2
(45) Date of Patent: Oct. 12, 2010

(54) VENTILATORY CONTROL SYSTEM

(75) Inventors: Stephen D. Pittman, Brookline, MA (US); Erik K. Witt, Murrysville, PA (US); Stefanida K. Blake, Jamacia Plain, MA (US)

(73) Assignee: RIC Investments, LLC, Wilmington, DE (US)

( * ) Notice: Subject to any disclaimer, the term of this patent is extended or adjusted under 35 U.S.C. 154(b) by 730 days.

(21) Appl. No.: 11/715,726

(22) Filed: Mar. 8, 2007

(65) Prior Publication Data
US 2007/0221224 A1 Sep. 27, 2007

Related U.S. Application Data

(60) Provisional application No. 60/784,127, filed on Mar. 20, 2006.

(51) Int. Cl.
*A62B 7/02* (2006.01)
(52) U.S. Cl. .................... 128/204.23; 128/204.18; 128/204.21; 128/914
(58) Field of Classification Search .......... 128/204.22, 128/200.24, 204.18, 204.21, 204.23, 204.25, 128/204.26, 204.28, 204.29, 205.11, 206.21, 128/914
See application file for complete search history.

(56) References Cited

U.S. PATENT DOCUMENTS

| | | | | |
|---|---|---|---|---|
| 4,326,513 A * | 4/1982 | Schulz et al. | ........... | 128/203.14 |
| 5,320,093 A * | 6/1994 | Raemer | ........... | 128/203.12 |
| 5,694,923 A | 12/1997 | Hete et al. | | |
| 5,752,509 A | 5/1998 | Lachmann et al. | | |
| 6,017,315 A | 1/2000 | Starr et al. | | |
| 6,532,959 B1 * | 3/2003 | Berthon-Jones | ........ | 128/204.23 |
| 6,615,830 B1 | 9/2003 | Serowski et al. | | |
| 6,752,150 B1 | 6/2004 | Remmers et al. | | |
| 6,752,151 B2 | 6/2004 | Hill | | |
| 6,799,570 B2 * | 10/2004 | Fisher et al. | ........... | 128/200.24 |
| 6,851,425 B2 | 2/2005 | Jaffre et al. | | |
| 7,520,279 B2 * | 4/2009 | Berthon-Jones | ........ | 128/204.21 |
| 7,533,670 B1 * | 5/2009 | Freitag et al. | .......... | 128/204.23 |
| 2002/0148466 A1 * | 10/2002 | Berthon-Jones | ........ | 128/200.24 |
| 2003/0000522 A1 | 1/2003 | Lynn et al. | | |
| 2003/0106553 A1 * | 6/2003 | Vanderveen | ........... | 128/204.18 |
| 2003/0172925 A1 * | 9/2003 | Zocca et al. | ........... | 128/202.22 |

(Continued)

OTHER PUBLICATIONS

PCT Search Report and Written Opinion, Dec. 18, 2007.

(Continued)

*Primary Examiner*—Justine R Yu
*Assistant Examiner*—LaToya Louis
(74) *Attorney, Agent, or Firm*—Michael W. Haas

(57) ABSTRACT

A system is provided for delivering a flow of breathing gas to an airway of a patient. The system includes a pressurizing flow module that generates a pressurized flow of breathing gas and a patient circuit coupled to the pressurizing flow module configured to communicate the flow of breathing gas to an airway of a patient. The system includes a sensor for monitoring a characteristic of a breathing pattern of the patient a controller that communicates with the sensor configured to increase a fraction of inspired carbon dioxide if the characteristic exceeds an upper threshold value and to provide servo-ventilation if the characteristic is less than a lower threshold value. The upper threshold value and the lower threshold value are changed based on the monitored characteristic of the breathing pattern of the patient.

20 Claims, 9 Drawing Sheets

U.S. PATENT DOCUMENTS

| | | | |
|---|---|---|---|
| 2003/0230308 A1* | 12/2003 | Linden | 128/204.18 |
| 2004/0134496 A1* | 7/2004 | Cho et al. | 128/204.23 |
| 2004/0144383 A1 | 7/2004 | Thomas et al. | |
| 2004/0187870 A1* | 9/2004 | Matthews et al. | 128/204.22 |
| 2004/0216740 A1* | 11/2004 | Remmers et al. | 128/204.18 |
| 2005/0039745 A1* | 2/2005 | Stahmann et al. | 128/204.18 |
| 2005/0065567 A1* | 3/2005 | Lee et al. | 607/17 |
| 2005/0279358 A1* | 12/2005 | Richey, II | 128/204.23 |
| 2006/0070624 A1* | 4/2006 | Kane et al. | 128/204.23 |
| 2007/0169776 A1 | 7/2007 | Kepler et al. | |

OTHER PUBLICATIONS

U.S. Appl. No. 11/481,323, filed Jul. 5, 2006, Pujol et al.

Lorenzi-Filho et al., "Effects of Inhaled Carbos Dioside and Oxygen on cheyne-Stokes Respiration in Patients with Heart Failure", American Journal of Respiratory and Critical Care Medicine 1999; 159:1490-1498.

* cited by examiner

VENTILATORY CONTROL SYSTEM

CROSS-REFERENCE TO RELATED APPLICATIONS

This application claims priority under 35 U.S.C. §119(e) from provisional U.S. patent application No. 60/784,127, filed Mar. 20, 2006, the contents of which are incorporated herein by reference.

BACKGROUND OF THE INVENTION

1. Field of the Invention

The present invention relates to the treatment of various forms of sleep disordered breathing, and, more particularly, to treating sleep disordered breathing with an adaptive, state-dependent positive airway pressure system.

2. Description of the Related Art

Sleep disordered breathing (SDB) is a common condition with important clinical consequences for affected individuals. Physicians and other experts have suggested that SDB exists as a continuum between a pure central apnea (caused by a lost drive to breathe) and a pure obstructive apnea (due to mechanics of the upper airway). Obstructive sleep apnea (OSA) is characterized by repetitive collapse of the upper airway during sleep as a result of lost compensation during sleep for an anatomic deficiency. This yields episodes of reduced airflow, hypoxemia (reduced oxygen level in the blood), hypercapnia (elevated circulating carbon dioxide, $CO_2$), and arousal from sleep to reestablish a stable airway. However, emerging data suggest that the pathophysiology of SDB is not limited to just collapse of the upper airway.

Respiration is the process where $O_2$-rich, $CO_2$-deficient air is brought into the lungs with diaphragm and/or thoracic muscle contraction so that $CO_2$ in the deoxygenated, $CO_2$-rich blood returning to the lungs can passively follow its concentration gradient and diffuse from the blood into the alveoli and $O_2$ can follow its concentration gradient from the alveoli into the blood. Respiration is regulated by negative feedback. The primary variable controlled by this system is $CO_2$ in the bloodstream, measured as the partial pressure of carbon dioxide, $PCO_2$. An increase in $PCO_2$ at central and peripheral chemoreceptors leads to a compensatory increase in ventilation (i.e., ventilation is used to rid the body of $CO_2$) and a decrease in $PCO_2$ at the chemoreceptors leads to a decrease in ventilation. In this way, $PCO_2$ is maintained within a physiological range by controlling ventilation. If the negative feedback of this system is compromised, then for a given ventilatory disturbance (e.g., increased ventilation with an arousal from sleep), the resulting ventilatory response may be amplified instead of damped. This can lead to episodes of hyperventilation followed by central apnea (a form of SDB that may have little to do with upper airway collapsibility).

The respiratory control system can be modeled as a system of compartments (brain compartment, lung compartment, etc.) interconnected by the vasculature. Carbon dioxide flows via the bloodstream between these compartments. The plant compartment describes the input-output relationship between ventilation and the $PCO_2$ in the lungs and consists of two sub-compartments, the lungs and the body tissues. The plant can be described by a system of nonlinear first order differential equations, but can be simplified using the concept of plant gain, which represents the change in alveolar partial pressure of carbon dioxide $P_ACO_2$ over the change in ventilation ($\Delta P_ACO_2/\Delta$ventilation). Under room air conditions, the plant gain determines the decrease in $P_ACO_2$ (thereby increasing the $CO_2$ concentration gradient between the blood and alveoli) for a given increase in ventilation. Thus, limiting the decrease in $P_ACO_2$ (i.e. decreasing the $CO_2$ concentration gradient) with ventilation by increasing the concentration of $CO_2$ in the alveoli lowers the gain of the plant compartment. Because the overall gain of ventilatory control is a product of all of the compartment gains, lowering the plant gain reduces the loop gain of the entire system and helps to dampen the response to a given disturbance.

Numerous studies have demonstrated that positive airway pressure administered with a patient interface, such as a mask, can effectively treat OSA when titrated to the appropriate pressure, and, in most cases, will also improve sleep architecture. Data also suggest there are significant clinical benefits to treating OSA. However, there are reasons to believe that poor adherence to therapy (i.e., ongoing time spent asleep at the prescribed continuous positive airway pressure (CPAP) is less than target) and significant residual SDB during therapy may have negative consequences regarding clinical outcomes.

Cheyne-Stokes respiration (CSR) is another form of sleep disordered breathing observed in some individuals with increased sensitivity to chemical respiratory stimuli. It is usually associated with heart failure, but may also be a comorbidity of some neurological conditions. FIG. 1 illustrates a typical Cheyne-Stokes respiration (CSR) pattern 30, which is characterized by rhythmic waxing periods 32 and waning periods 34 of respiration, with regularly recurring periods of high respiratory drive (hyperpnea) 36 and low respiratory drive (hypopnea or apnea) 38. A typical Cheyne-Stokes cycle, generally indicated at 40 in FIG. 1, lasts about one minute and is characterized by a crescendo (arrow A), in which the peak respiratory flow of the patient increases over several breath cycles, and decrescendo (arrow B) variation in peak flow, in which the peak respiratory flow of the patient decreases over several breath cycles. The disruption in sleep, as well as the periodic desaturation of arterial oxygen ($PO_2$), stresses the cardio-vascular system and specifically the heart. Hyperpnea often causes arousals and, thus, degrades sleep quality.

Emerging data suggest that an adaptive algorithm that can provide non-invasive mechanical ventilation when central apneas are detected and support ventilation when the instantaneous peak airflow falls below an adaptive threshold can significantly reduce or even eliminate CSR by augmenting ventilation during a state of low respiratory drive.

Others have shown in independent studies that CSR can be significantly reduced and even eliminated in the laboratory with inhaled $CO_2$ or added dead space to promote rebreathing of $CO_2$ (i.e., interventions to reduce the plant gain). FIG. 2, from Lorenzi-Filho G., Rankin F., Bies I., Bradley T. D.; *Effects of Inhaled Carbon Dioxide and Oxygen of Cheyne-Stokes Respiration in Patients with Heart Failure*, American Journal of Respiratory and Critical Care Medicine 1999; 159: 1490-1498, hereby incorporated by reference in its entirety, shows the elimination of CSR and central apneas by inhalation of $CO_2$ (sample B) compared to the breathing of air (sample A). As shown in FIG. 2, various measurements were taken in the study to show the effects of $CO_2$ and $O_2$ inhalation including electroencephalogram (EEG), submental electromyogram (EMG), tidal volume ($V_T$), saturation of oxygen ($SaO_2$), fraction of end tidal carbon dioxide ($F_{ET}CO_2$), and transcutaneous partial pressure of carbon dioxide ($PtcCO_2$).

There has also been success in treating CSR in a small outpatient-based, intention-to-treat trial of low-flow CPAP that promotes rebreathing of $CO_2$. U.S. Pat. No. 6,752,150 to Remmers et al. ("the '150 patent"), which is hereby incorporated by reference in its entirety, discloses a modified continuous positive airway pressure (CPAP) system designed to promote rebreathing of $CO_2$ to treat central apneas. Furthermore, the benefit of improving ventilatory control may be generalized beyond those with CSR or central apneas. Individuals with obstructive sleep apnea (OSA) that demonstrate CPAP emergent central apneas appear to have issues with both upper airway collapsibility and ventilatory control. Thus, stabilizing the upper airway with positive airway pressure and decreasing the plant gain by increasing the concentration of alveolar $CO_2$ during episodes of hyperventilation may improve the efficacy of positive pressure therapy in these individuals. In individuals with a stable upper airway, an intervention to decrease the plant gain may be adequate without the use of positive airway pressure.

U.S. patent application Ser. No. 10/716,360 (Publication No. US 2004/0144383 A1) ("the '360 application"), which is hereby incorporated by reference in its entirety, discloses a system and method for treating sleep disordered breathing by providing precise concentrations of $CO_2$ and $O_2$ to the patient in conjunction with positive airway pressure. A supplemental source of $CO_2$ is provided and mixed with a supply of $O_2$ before being supplied to the patient. This configuration thus addresses the sleep disordered breathing problems relating to upper airway obstruction as well as abnormal control of breathing (e.g., CSR) since it maintains the positive airway pressure flow.

Bi-level positive airway pressure therapy is a form of positive airway pressure therapy that has been advanced in the treatment of sleep apnea and other breathing and cardiac disorders. In bi-level therapy, pressure is applied to the airway of a patient alternately at relatively higher and lower pressure levels so that the therapeutic pressure is alternately administered at a larger and smaller magnitude force. The higher and lower magnitude positive prescription pressure levels are known as inspiratory positive airway pressure (IPAP) and expiratory positive airway pressure (EPAP), and are synchronized with the patient's inspiratory cycle and expiratory cycle, respectively.

An adaptive form of bi-level therapy, known as variable positive airway pressure (VarPAP), is disclosed in U.S. Pat. No. 6,752,151 to Hill ("the '151 patent"), which is hereby incorporated by reference in its entirety. The VarPAP system implements many of the standard functions of a positive airway pressure support device, as well as an algorithm that adjusts IPAP, EPAP, or both in order to counter a CSR pattern. A flow sensor is utilized to determine the patient's peak flow during respiratory cycles, which allows a controller to monitor the peak flows to determine whether the patient is experiencing CSR other sleep disordered breathing. The algorithm involves a three-layer process, each occurring at different time intervals, in order to continually adapt the supplied gas pressure to suit the patient's needs and to detect any occurrences of sleep disorders. In the event of a hypopnea or apnea period, known as central apneas as described above, the VarPAP according to the disclosed system may provide a "machine breath" in order to stimulate respiration in the patient.

Another disclosure, pending U.S. application Ser. No. 11/235,520 (Publication No. US 2006/0070624) ("the '520 application"), which is hereby incorporated by reference in its entirety, aims to improve upon the '151 patent and makes determinations based on the parameters of instantaneous average inspiratory flow and maximum average inspiratory flow. These averaged parameters serve to smooth out or filter the direct instantaneous parameters used in the '151 patent and may therefore lead to smoother results. Further improvements are made relating to the monitoring of intra-breath flow and enhanced disorder detection.

SUMMARY OF THE INVENTION

In accordance with an aspect of the present invention, a system is provided for delivering a flow of breathing gas to an airway of a patient. The system includes a pressurizing flow module that generates a pressurized flow of breathing gas and a patient circuit coupled to the pressurizing flow module configured to communicate the flow of breathing gas to an airway of a patient. The system includes a sensor for monitoring a characteristic of a breathing pattern of the patient a controller that communicates with the sensor configured to increase a fraction of inspired carbon dioxide if the characteristic exceeds an upper threshold value and to provide servo-ventilation if the characteristic is less than a lower threshold value. The upper threshold value and the lower threshold value are changed based on the monitored characteristic of the breathing pattern of the patient.

In accordance with another aspect of the present invention, a system is provided for delivering a flow of breathing gas to an airway of a patient and includes a pressurizing flow module that generates a flow of breathing gas and a patient circuit coupled to the pressurizing flow module configured to communicate the flow of breathing gas to an airway of a patient. The system further includes a sensor for monitoring a characteristic of a breathing pattern of the patient and a carbon dioxide supplement system associated with said patient circuit. A controller is operatively connected with the pressurizing flow module and carbon dioxide supplement system. The controller communicates with the sensor and increases an amount of carbon dioxide in the patient circuit for inspiration by the patient if the characteristic exceeds an upper threshold value and controls the gas flow generator module to increase a ratio of inspiratory pressure to expiratory pressure provided to the airway of the patient if the characteristic is less than a lower threshold value.

In accordance with another aspect of the present invention a method for determining states of ventilation of a patient undergoing respiratory therapy is provided. In the method, a flow of gas is delivered to the airway of the patient from a source of breathing gas via a patient circuit and a characteristic of a breathing pattern of a patient is monitored. A lower threshold value is established for the characteristic based on a mean value of the characteristic over a period of time and an upper threshold value is established for the characteristic by increasing or decreasing an initial value for the characteristic. The upper threshold value is decreased if a change in the mean value of the characteristic exceeds a predetermined limit, and the upper threshold value is increased if a frequency of a particular therapy supplied to the patient exceeds a predetermined frequency.

According to another aspect of the present invention, a method for treating a patient is provided in which a flow of gas is delivered to the airway of the patient from a source of breathing gas via a patient circuit and a characteristic of the breathing pattern of the patient is monitored. A state of high respiration is predicted if a change in the characteristic over a period of time is a positive value and exceeds a predetermined limit, and a state of low respiration is predicted if the change in the characteristic over a period of time is a negative value which has an absolute value that exceeds the predetermined limit. An appropriate treatment is applied to the patient based on the predicted state.

According to another aspect of the present invention, a method of delivering pressurized breathing gas to an airway of a patient is provided. A flow of gas is delivered to the airway of the patient from a source of breathing gas via a patient circuit and a characteristic of the breathing pattern of the patient is monitored. An upper threshold value of the characteristic and a lower threshold value of the characteristic are determined based on the breathing pattern of the patient and the fraction of inspired carbon dioxide is increased if the value of the characteristic exceeds the upper threshold.

According to another aspect of the present invention, a method for determining an ideal therapeutic window in the treatment of a patient is provided. A dose of an appropriate treatment is applied to the patient based on a predicted or existing state of respiration and an index of instability of the patient in response to the applied dose is measured. A series of data points are recorded, representing the indices of instability for each of a series of responses and a therapeutic window is fitted that corresponds the applied dose with the index of instability below the data points for which the measured index of instability exceeds an acceptable value and above the data points for which the measured index of instability is below an acceptable value.

According to another aspect of the present invention, a method is provided for treating a patient within an ideal therapeutic window in which a dose of an appropriate treatment is applied to the patient based on a predicted or existing state of respiration. An index of instability of the patient in response to the applied dose is measured and a series of data points representing the indices of instability for each of a series of responses is recorded. A therapeutic window is fitted that corresponds the applied dose with the index of instability below the data points for which the measured index of instability exceeds an acceptable value and above the data points for which the measured index of instability is below an acceptable value. Subsequent doses of treatment within the therapeutic window are applied to the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Individuals demonstrating central sleep apnea, Cheyne-Stokes respiration, CPAP emergent central apneas, or other forms of breathing that indicate unstable control of breathing appear to have an elevated loop gain that describes the ventilatory response to a given ventilatory stimulus. The primary contributor to this elevated loop gain is likely an increased sensitivity to carbon dioxide ($CO_2$) by central chemoreceptors (elevated controller gain). The present invention describes a method to counteract this elevated loop gain by lowering the ventilatory plant gain during a state of high respiratory drive and augmenting ventilation during a state of low respiratory drive.

Figure 3:
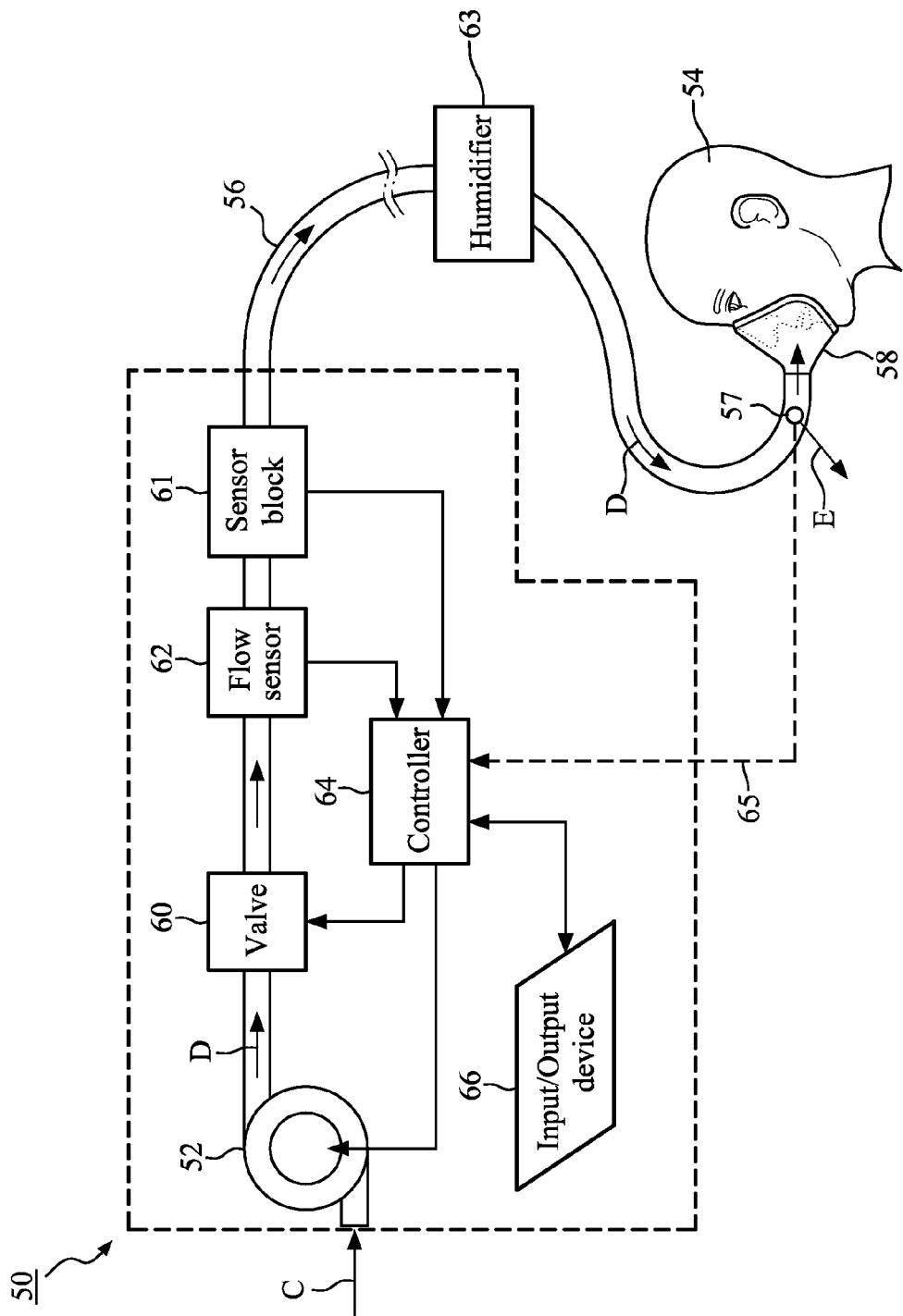
FIG. 3 is a schematic representation of an apparatus in accordance with an embodiment of the present invention.

The functional elements of the apparatus used in the present invention may be similar to those disclosed in the '151 patent. As shown in FIG. 3, a state-dependent positive airway pressure support system 50 includes a gas flow generator 52, such as a blower used in a conventional CPAP or bi-level device, that receives breathing gas, generally indicated by arrow C, from any suitable source, e.g., a pressurized tank of oxygen or air, the ambient atmosphere, or a combination thereof. Gas flow generator 52 generates a flow of breathing gas, such as air, oxygen, or a mixture thereof, for delivery to an airway of a patient 54 at relatively higher and lower pressures, i.e., generally equal to or above ambient atmospheric pressure. Oxygen may be delivered to the patient in order to prevent oxyhemoglobin desaturation that may result from the hypoventilation associated with a low respiratory drive state and/or to stabilize respiratory control independent of the oxyhemoglobin saturation status.

The pressurized flow of breathing gas, generally indicated by arrow D from gas flow generator 52 is delivered, via a delivery conduit 56, to a breathing mask or patient interface 58 of any known construction, which is typically worn by or otherwise attached to a patient 54 to communicate the flow of breathing gas to the airway of the patient. Delivery conduit 56 and patient interface device 58 are collectively referred to as a patient circuit. An exhaust vent 57 for exhausting air indicated by arrow E may be included in the patient interface 58, the conduit 56, or any other suitable location. In one embodiment, the exhaust vent 57 may comprise an adjustable valve to alter the pressure bias in the patient circuit so as to increase or decrease captured exhaled gas (and particularly $CO_2$) for rebreathing purposes. The valve may be manually adjustable or may be automatically controlled by a controller 64 via operative link 65, as discussed below. The apparatus according to the present invention may be a one- or two-limb system, as described in the '151 patent, or may contain more than two limbs.

In one embodiment, some or all of the various sections of conduit 56 may be provided by flexible tubing, rigid tubing, or by other members that would provide a conduit for the breathable gas therethrough. Patient interface 58 is any appliance, either invasive or non-invasive, such as a nasal mask, nasal/oral mask, total face mask, nasal cannula, endotracheal tube, or tracheal tube, suitable for communicating a supply of breathable gas to the airway of a patient. The patient interface 58 may include headgear for mounting the appliance on the head of a patient. In addition, the patient interface 58 may include controls mounted thereon for controlling at least one aspect of the patient treatment system. In the illustrated embodiment, patient interface 58 and/or conduit 56 includes a suitable exhaust port 57 for exhausting gas from these components to ambient atmosphere. Exhaust port 57 may be a passive exhaust port in the form of a continuously open port that imposes a flow restriction on the exhaust gas to permit control of the pressure of gas within patient interface 58. Alternatively, exhaust port 57 may be an active exhaust port that assumes different configurations to control the exhaust rate. The exhaust port 57 may communicate with the controller 64 via operative link 65 so that it is automatically and/or dynamically controlled by the system. Examples of suitable exhaust ports are taught, for example, in U.S. Pat. Nos. 6,851,425 and 6,615,830, the contents of which are hereby incorporated by reference into the present application.

In the illustrated embodiment, the state-dependent positive airway pressure support system includes a pressure controller in the form of a valve 60 provided in delivery conduit 56. Valve 60 controls the pressure of the flow of breathing gas from flow generator 52 delivered to the patient. For present purposes, flow generator 52 and valve 60 are collectively referred to as a pressurizing flow module because they act in concert to control the pressure and/or flow of gas delivered to the patient.

Referring to FIG. 3, the pressurizing flow module, which includes the flow generator 52 and valve 60, is illustrated according to one embodiment of the invention. In the embodiment illustrated in FIG. 3, pressurizing flow module includes a flow generator 52 that receives the breathable gas and elevates the pressure of that gas for delivery to the airway of a patient. Flow generator 52 is any device, such as a pump, blower, piston, or bellows that is capable of elevating the pressure of the received breathable gas for delivery to a patient. As mentioned above, the present invention also contemplates that gas other than ambient atmospheric air may be introduced into the system for delivery to the patient. In such embodiments, a pressurized canister or tank of gas containing air, oxygen, carbon dioxide, or other breathable gas mixture can supply the intake to flow generator 52. In another embodiment of the pressurizing flow module, flow generator 52 need not be provided, but instead the breathable gas can be pressurized by the pressure of the canister or tank of pressurized gas itself, with the pressure delivered to the patient being controlled by a pressure regulator. In one embodiment, flow generator 52 is a blower that is driven at a substantially constant speed during the course of the pressure support treatment to provide the gas in the system with a substantially constant elevated pressure and/or flow rate.

In the embodiment of FIG. 3, the breathable gas in the pressurizing flow module is directed from flow generator 52 to a control valve 60. As is described below, control valve 60 and/or pressure generator 52 form the pressurizing flow module that controls the circuit pressure and/or the circuit flow rate of the gas in the circuit downstream from the pressurizing flow module. Examples of control valve 60 include at least one valve, such as sleeve or poppet valve, that exhausts gas from circuit 12 as a method of controlling the circuit pressure and circuit flow rate. U.S. Pat. No. 5,694,923 to Hete et al., the contents of which are incorporated herein by reference, teaches a dual poppet valve system suitable for use as control valve 60 that exhausts gas to atmosphere and restricts the flow of gas from flow generator 52 to the patient.

For embodiments in which flow generator 52 is a blower that operates at only one speed, then one or more control settings of control valve 60 can be adjusted to provide control over the circuit pressure and the circuit flow rate for the breathable gas in the circuit. However, the present invention also contemplates embodiments in which one or more control settings related to the operation of flow generator 52, such as a blower speed, are adjusted alone or in combination with the control settings of control valve 60 to control the circuit pressure and the circuit flow rate for the breathable gas delivered to the patient along. For example, a circuit pressure and a circuit flow rate close to the desired circuit pressure and circuit flow rate can be set by adjusting an appropriate operating speed for flow generator 52 (macro control). Fine tuning (micro control) of the circuit pressure and the circuit flow rate can then be provided by adjusting one or more control settings associated with control valve 60 so that the two, operating together, determine the final circuit pressure for the breathable gas in the circuit downstream from the pressurizing flow module.

It should be apparent that other techniques for controlling the pressure delivered to the patient by the pressurizing flow module, such as varying the blower speed, either alone or in combination with a pressure control valve 60, are contemplated by the present invention. Thus, valve 60 is optional depending on the technique used to control the pressure of the flow of breathing gas delivered to the patient. If valve 60 is eliminated, the pressurizing flow module corresponds to flow generator 52 alone, and the pressure of gas in the patient circuit is controlled, for example, by controlling the motor speed of the flow generator 52. A further technique for controlling pressure is to bleed flow to the atmosphere, or into another limb of the circuit using active or passively controlled valves.

State-dependent positive airway pressure support system 50 further includes a flow sensor 62 that measures the flow of breathing gas within delivery conduit 56. Flow sensor 62 is any device suitable for measuring these parameters, such as a spirometer, pneumotach, variable orifice transducer, differential pressure transducer, or other conventional flow transducer. In accordance with a presently preferred embodiment shown in FIG. 3, flow sensor 62 is interposed in line with delivery conduit 56, most preferably downstream of valve 60. Flow sensor 62 generates a flow signal that is provided to a controller 64 and is used to determine the flow of gas at the patient.

Of course, other techniques for measuring the respiratory flow of the patient are contemplated by the present invention, such as measuring the flow directly at the patient or at other locations along delivery conduit 54, measuring patient flow based on the operation of the pressure generator, and measuring patient flow using a flow sensor upstream of the pressure generator. For example, U.S. Pat. No. 6,017,315 to Starr et al., the contents of which are incorporated herein by reference, teaches a quantitative flow member that is located at patient interface. Flow can also be derived from other indirect parameters measured in the system, such as pressure, temperature, $CO_2$ concentration, etc.

A further sensor block 61 is provided in the circuit shown in FIG. 3. The sensor block 61 may represent one or several additional sensors that may detect $CO_2$, $O_2$ (main stream or side stream), or some other suitable measure, in order to gather information relating to the properties of the gas being delivered to or exhaled by the patient. The various sensors need not be located at the same location along the delivery apparatus, rather, sensor block 61 is merely representative of the sensors that may be distributed along the apparatus. As such, $CO_2$ measurements may be implemented in the patient interface 58, the conduit 56, or anywhere else in the unit and are not intended to be limited to within the pressure supply circuit 50; they may be in the patient circuit as well. The measurements can be used in algorithms to determine the amount of $CO_2$ in a reservoir or dead space. The measurements can additionally be used to determine how much $CO_2$ retention or wash-out has occurred, which can predict the onset of clinically undesired respiratory drive states. This information can be used to drive therapy decision-making. The sensors may calculate washout or stored $CO_2$ by integrating the measured $CO_2$ levels that flow past a sensor multiplied by the flow over time during inspiration or expiration. The measurements may be taken directly or indirectly.

The system may additionally include a humidifier 63. Although shown as being located in the patient circuit in FIG. 3, it is to be understood that the humidifier 63 may be located anywhere else in the gas supply system, such as in the positive airway pressure circuit 50. The humidifier 63 further improves comfort by providing moisture in the supplied gas. The humidifier may be configured to not only increase humidification, but to also take moisture out of the conduit 56 due to rebreathing exhaled moist air. Thus, the humidifier 63 may either be a passover or heated humidifier or a subsystem which controls humidity (adding or removing humidity). Pending U.S. patent application Ser. No. 11/234,351 (Publication No. US 2007/0169776, incorporated herein by reference in its entirety, discloses a humidifier device suitable for use in the present invention. In addition, pending U.S. patent application Ser. No. 11/481,232, incorporated herein by reference in its entirety, discloses such a humidifier device for controlling the level of moisture within a ventilator circuit.

An input/output device 66 is provided for setting various parameters used by the state-dependent positive airway pressure support system, as well as for displaying and outputting information and data to a user, such as a clinician or caregiver. It is to be understood that the present invention contemplates providing input/output terminals so that the operation information and data collected by the state-dependent positive airway pressure support system can be monitored and controlled remotely. Input/output device 66 may be any device suitable to provide information and/or commands to controller 64 via an operative link and to present information to the patient, or another user, in a human perceivable format. Examples of a suitable input/output device includes a keypad, keyboard, touch pad, mouse, visual display (e.g., LCD or LED screen), microphone, speaker, switches, button, dials, lamps, or any other devices that allow a user to input information to and receive information from the ventilation system.

Controller 64 is preferably a microprocessor that is capable of implementing and executing routines for monitoring characteristics of patient respiration and controlling the flow of breathing gas based thereon as discussed in detail below. The controller 64 is operatively linked to the pressurizing flow module (flow generator 52 and valve 60). For example, in the embodiment of FIG. 3, the output of sensors 61 and 62 may be provided to controller 64, which comprises a processor for determining the instantaneous volume (V) of gas delivered to the patient, or the instantaneous flow rate (V') of such gas to the patient, or both. For example, the instantaneous volume can be determined by integrating the measured flow rate from sensor 62. In embodiments wherein the flow sensor 62 is located relatively far from patient interface 58, in order to determine the actual flow rate of gas to the patient or the actuation flow rate of gas from the patient, which is considered a negative flow, controller 64 receives the output from sensor 62 as an estimated flow. Controller 64 processes this estimated flow information, for example, by performing leak estimation, to determine the actual flow at the patient's airway, as is known to those skilled in the art.

Figure 4:
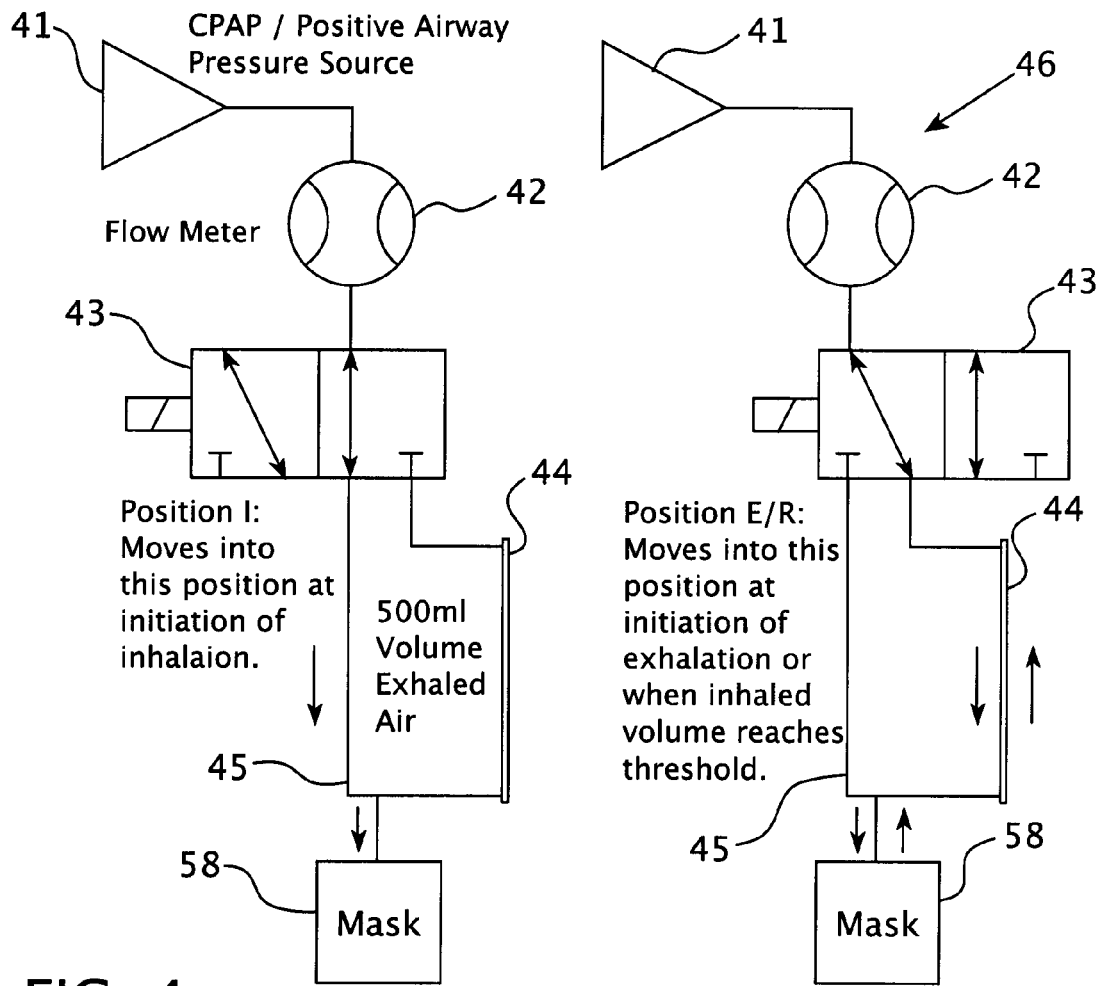
FIG. 4 is a schematic representation of a rebreathing circuit in accordance with an embodiment of the present invention.

An example of a suitable rebreathing circuit 46 for containing exhaled $CO_2$ and redelivery to the patient is depicted in FIG. 4. The rebreathing circuit 46 may be integrated with the circuit shown in FIG. 3. The rebreathing circuit 46 receives pressured gas from pressure source 41, which may be the pressurizing flow module as described and includes a flow meter 42. The rebreathing circuit 46 includes a 3-port 2 position valve 43 that may be controlled by the controller 64 or potentially the CPAP or bi-level device itself (i.e., controlled by the flow of the gas). The valve 43 can be in one of two states. During inhalation (Position I; shown on the left side of FIG. 4), the valve 43 is in a first position and the circuit 46 is very similar to a traditional CPAP or bi-level pressure support system. However, there is a flow meter 42 in series with the circuit 46 and the flow meter 42 may provide a real-time value for airflow or inspired volume (by integrating the amount of airflow). During exhalation (Position E/R; shown on the right side of FIG. 4), the valve 43 moves to the second position, where expired air is directed into a tube-like circuit that has a reservoir 44 for collecting the exhaled gas, for example, 500 ml. During inhalation, should the inspired volume or flow exceed a preset level, the valve 43 will be moved to the E/R position, thus pressurizing the contained exhaled air, and delivering this to the patient. Trigger signals may be provided by suitable algorithms at the initiation of exhalation and inhalation. Additionally, an algorithm could be implemented that could determine a baseline inspired volume threshold, thus eliminating the need for a preset or predetermined inspired volume. Such an algorithm may be configured to adapt to the patient's needs.

Three states of respiration are defined by the present invention and are delineated by two dynamic and adaptive quantitative limits: an upper threshold and a lower threshold. The upper and lower threshold values may relate to a suitable characteristic indicating respiratory drive, such as peak airflow, an averaged peak flow, tidal volume, etc. When the indicating characteristic of a patient is between the upper and lower thresholds, the patient may be considered to be ventilating normally. When the indicating characteristic of a patient exceeds the upper threshold value, the patient is considered to be in a state of high respiratory drive. When the indicating characteristic of a patient falls below the lower threshold value, the patient is considered to be in a low respiratory drive state. A low respiratory drive state may be indicative of a central apnea, hypoventilation, or other sleep disordered breathing. Periods of high respiratory drive followed by low respiratory drive may be indicative of CSR. The state-dependent positive airway pressure system of the present invention applies varying interventions or therapies to a patient depending on the particular respiratory state the patient is in and, further, applies such interventions or therapies at adaptive intensity levels depending upon the severity of the state (i.e., how far the patient's respiration is from ideal).

It should be understood by those having skill in the art that, since the threshold values are dynamic, they may under certain conditions converge so as to shrink the window of normal respiration or to eliminate it altogether. In the case wherein the window of normal respiration becomes very small or nonexistent, the state-dependent positive airway pressure system of the present invention effectively continuously varies the appropriate intervention (e.g., increased doses of $CO_2$ or $O_2$, or adaptive servo-ventilation, as further discussed below) in proportion to the deviation from a target (i.e., in proportion to the severity of the respiratory state as determined from the deviation from the merged thresholds). The present disclosure primarily refers to the system as identifying three distinct states, but it is appreciated that in all cases the thresholds may converge and result in a system that effectively applies an appropriate intervention in an appropriate intensity based upon the deviation of an indicating characteristic from a single value.

Figure 5:
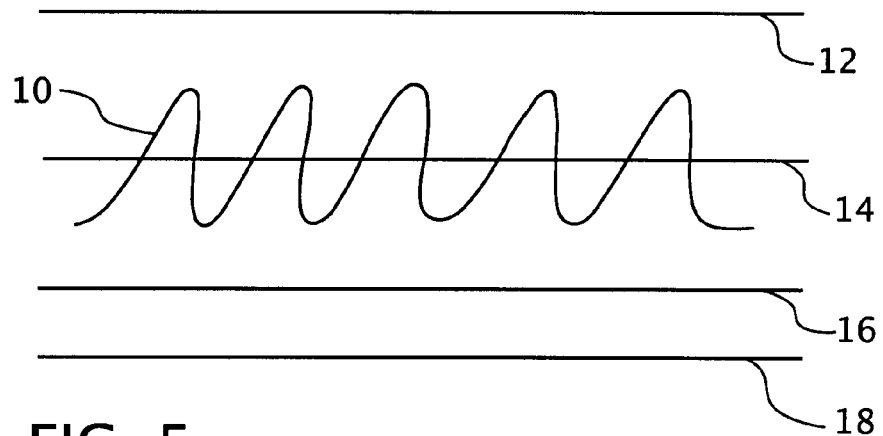
FIG. 5 is a graphical representation of a normal state of respiration in accordance with an embodiment of the present invention.

During the normal state of ventilation, that is, when the indicating characteristic of the patient is between the upper and lower thresholds, positive pressure therapy is delivered and is determined by prescribed CPAP or bi-level settings during a sleep study or by an automated algorithm to eliminate evidence of upper airway obstruction. The normal state of ventilation is shown in FIG. 5, which depicts patient airflow over time. One of skill in the art would recognize that tidal volume or another characteristic may alternatively be used in the present invention as an indicator. A peak flow upper threshold 12 and a peak flow lower threshold 14 are determined (as discussed below) and, in the normal state as shown, the actual airflow 10 of the patient peaks between the two thresholds.

As shown in FIG. 5, the bi-level therapy, including the inspiratory positive airway pressure 16 (IPAP) and the expiratory positive airway pressure 18 (EPAP), remains constant during the normal state. In an apparatus utilizing CPAP therapy (not shown) instead of bi-level therapy, the continuous pressure level delivered to the patient would likewise be constant. Known methods of expiratory pressure relief such as that provided by a C-Flex or Bi-Flex device, which reduce the expiratory pressure at the beginning of the expiratory breath, may also be incorporated to improve patient comfort. A Bi-Flex device also controls the inspiratory pressure based on the flow of gas monitored by the system.

Figure 6:
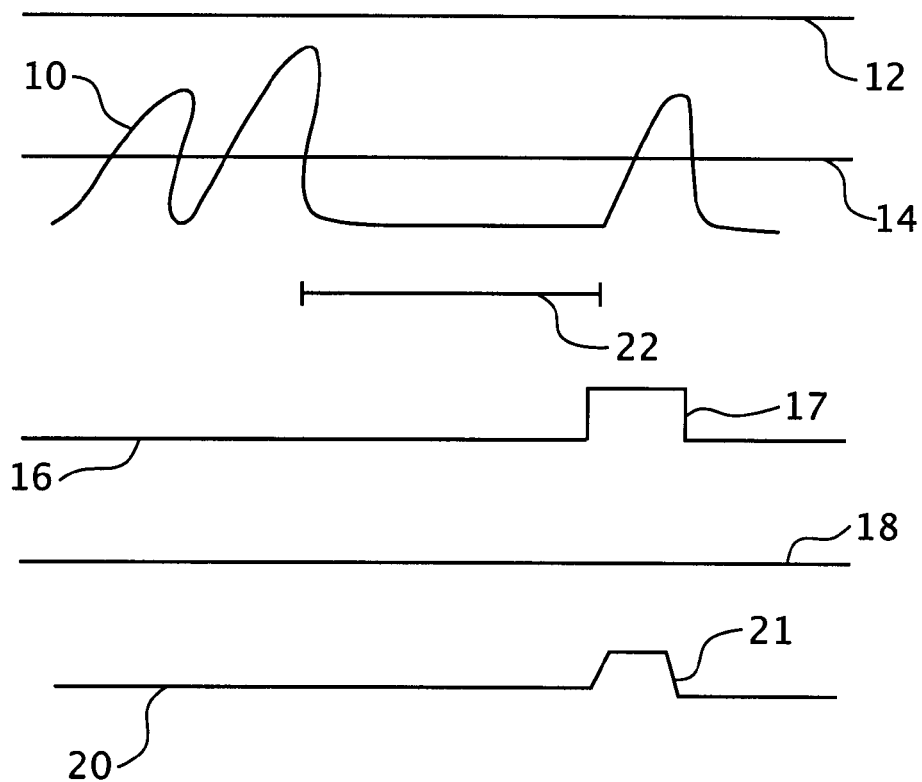
FIG. 6 is a graphical representation of a state of low respiratory drive in accordance with an embodiment of the present invention.

If the patient were to undergo a central apnea 22, as shown in FIG. 6, there would be no detectable airflow 10 from the patient and the peak airflow would thus fall below the lower threshold 14. The controller 64 receives the flow information from the flow sensor 62 and/or other sensors 61, compares it with the current threshold parameters and makes the determination that the patient is in a low respiratory drive state. The determination may be made after a fixed period of time in which no respiratory activity is detected or it may be made adaptively based on historical breathing patterns.

In the low state, the therapy delivered by the state-dependent positive airway pressure system shifts from the minimal therapy of CPAP or bi-level therapy, as applied during the normal state. It should be noted that the terms CPAP or bi-level therapy are used for descriptive purposes, but other therapeutic modes or methods intended to treat apneas with an obstructive component are contemplated in the invention, such as proportional assist ventilation (PAV) that attempt to delivery a flow of based on the patient's respiratory effort. In addition to the prescribed CPAP or bi-level therapy, the state-dependent positive airway pressure system may deliver servo-ventilation, or variable positive airway pressure (VarPAP), in order to generate a breath for the patient. An adaptive system for providing variable positive airway pressure to a patient based on recent breathing pattern history is disclosed in the '151 patent and is incorporated herein by reference in its entirety. A variable positive airway pressure system that uses time averaged parameters is disclosed in the '520 application and is also incorporated herein by reference in its entirety.

In servo-ventilating the patient, the controller 64, communicating with the flow generator 52 and/or control valve 60, increases the IPAP to EPAP pressure ratio such that the positive airway pressure system helps maintain spontaneous breathing by the patient (i.e., the patient ventilating on his or her own; known as "synchronous mode") or, in cases of central apnea wherein there is no spontaneous patient breathing, provides a "machine breath" in order to trigger spontaneous breathing. Providing a series of machine breaths according to controlled time intervals independent of the patient's activity is referred to as "time mode" and is also considered to be an element of servo-ventilation. In "combination mode," servo-ventilation is provided so as to help the patient breathe during spontaneous breathing as in synchronous mode and to provide machine breaths or timed control of breathing when the patient requires such control. As the severity of the condition lessens, the IPAP to EPAP pressure ratio may be decreased accordingly. As is known in the art, altering the change in pressure between IPAP and EPAP may be carried out by increasing/decreasing IPAP, decreasing/increasing EPAP, or both. For example, to increase the IPAP to EPAP ratio, the IPAP can be increased, the EPAP can be decreased, or both can be performed. The change may be effectuated across an entire breath or varyingly within a breath according to a predetermined or adaptive waveform.

As shown in FIG. 6, a central apnea 22 is detected after a period of time (which may be a preprogrammed period or adaptively determined) and a response 17 thereto is provoked. In the scenario depicted in FIG. 6, the response 17 is an increase in the inspiratory positive airway pressure (IPAP), or a "machine breath," that is intended to stimulate spontaneous breathing by the patient. Subsequent machine breaths may be delivered to the patient at intensity levels and time intervals determined as necessary based on patient history and/or current status.

In the low respiratory drive state, it may additionally be desirable to boost alveolar $CO_2$ ($PCO_2$) or the fraction of inspired $CO_2$ ($FiCO_2$) to increase ventilation. Various methods are known in the art to effectuate the increase of $CO_2$ including controlling rebreathing by an active leak valve, dynamically increasing dead space, providing a reservoir of exhaled $CO_2$, or providing a supplemental source of $CO_2$. The '150 patent, hereby incorporated by reference, discloses some of these mechanisms including an active leak valve, dynamic dead space, a reservoir of exhaled $CO_2$ and an adjustable mask exhaust valve, and is hereby incorporated by reference in its entirety. The '360 application discloses a supplemental source of $CO_2$ being mixed with $O_2$ and is incorporated by reference in its entirety as well. Other methods of creating higher levels of $CO_2$ than are present in the atmosphere are contemplated such as chemical generation, cryogenic cooling, molecular adsorption, and filtration of atmospheric gas, or exhaled gas from the patient.

Figure 7:
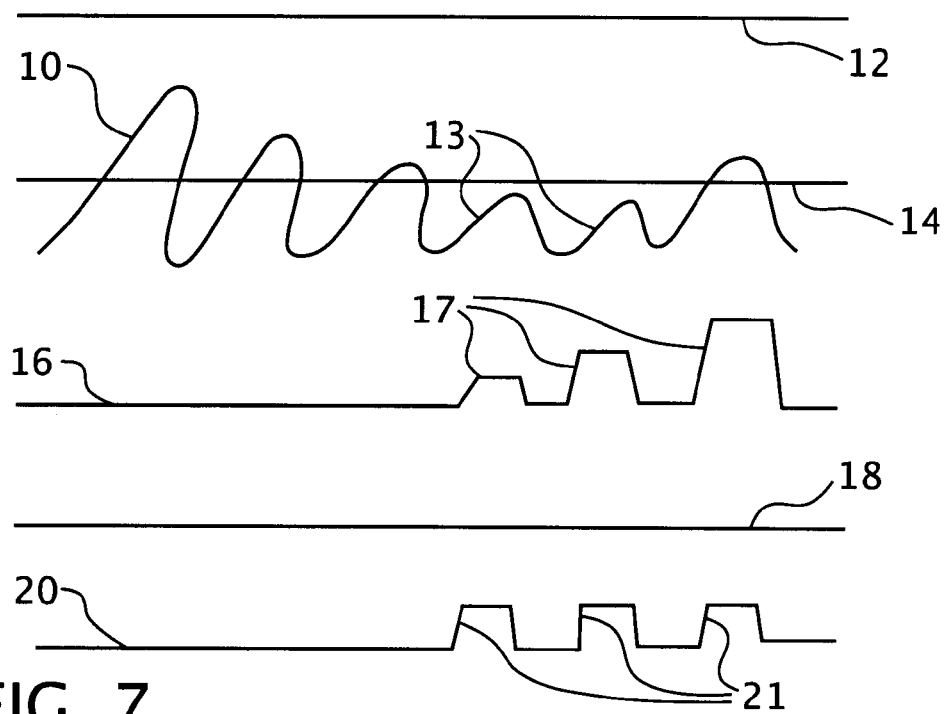
FIG. 7 is a graphical representation of a state of low respiratory drive in accordance with another embodiment of the present invention.

FIG. 7 shows the detection of a low respiratory drive state similar to that shown in FIG. 6 except that a small amount of ventilation is detected. In this case, the peak airflow of respiration 13 falls below the lower threshold value 14 and the controller 64 therefore declares a low respiratory state. As described above, the controller 64 provides the additional therapy of servo-ventilation (VarPAP) to boost the patient's respiratory drive. As shown in FIG. 7, the IPAP 16 may be adaptively increased 17 during spontaneous breathing, as described in the '151 patent, in response to the detected hypopnea. Methods to boost the $FiCO_2$ or alveolar $CO_2$ may also be implemented as described above (i.e., dynamic dead space, $CO_2$ reservoir, active leak valve, etc.) to boost the patient's respiratory drive, as indicated by the increases 21 in $FiCO_2$ control 20.

Figure 1:
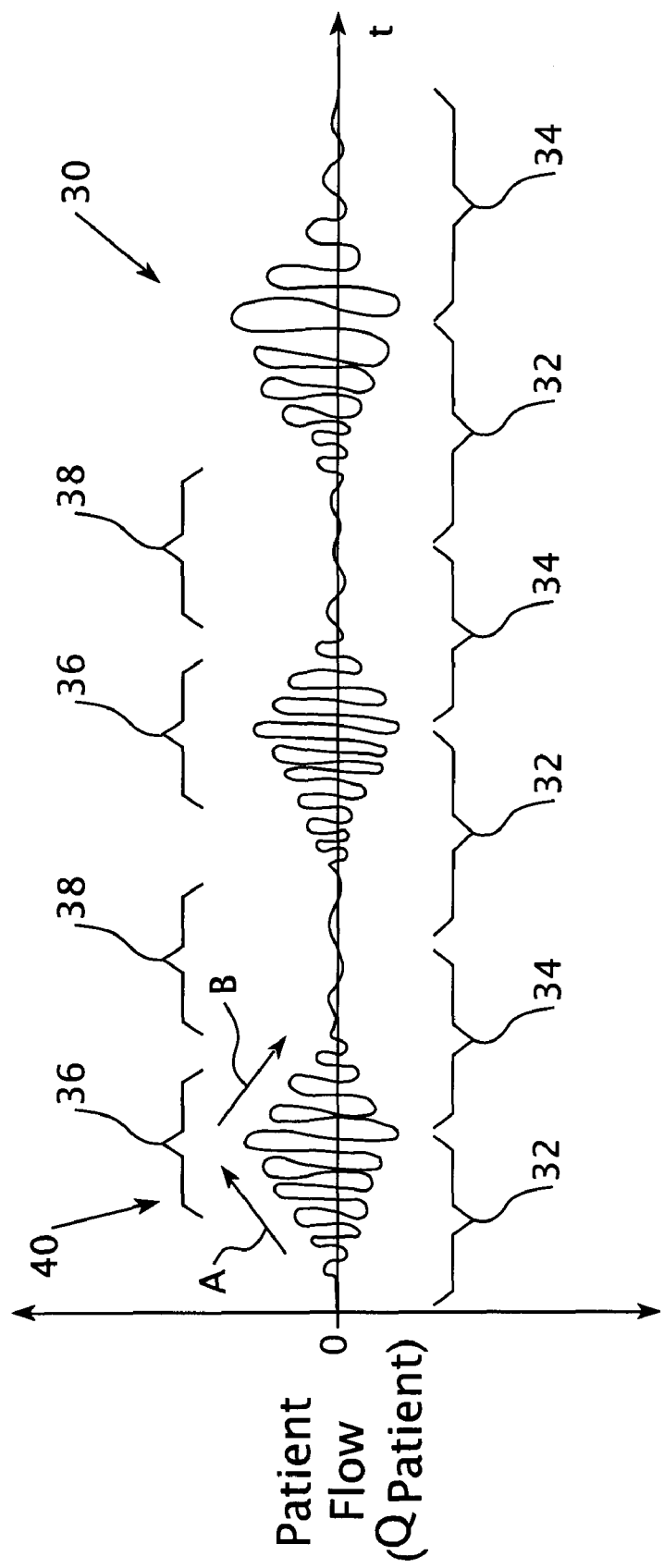
FIG. 1 shows a typical Cheyne-Stokes respiration pattern including waxing periods and waning periods.
Figure 2:
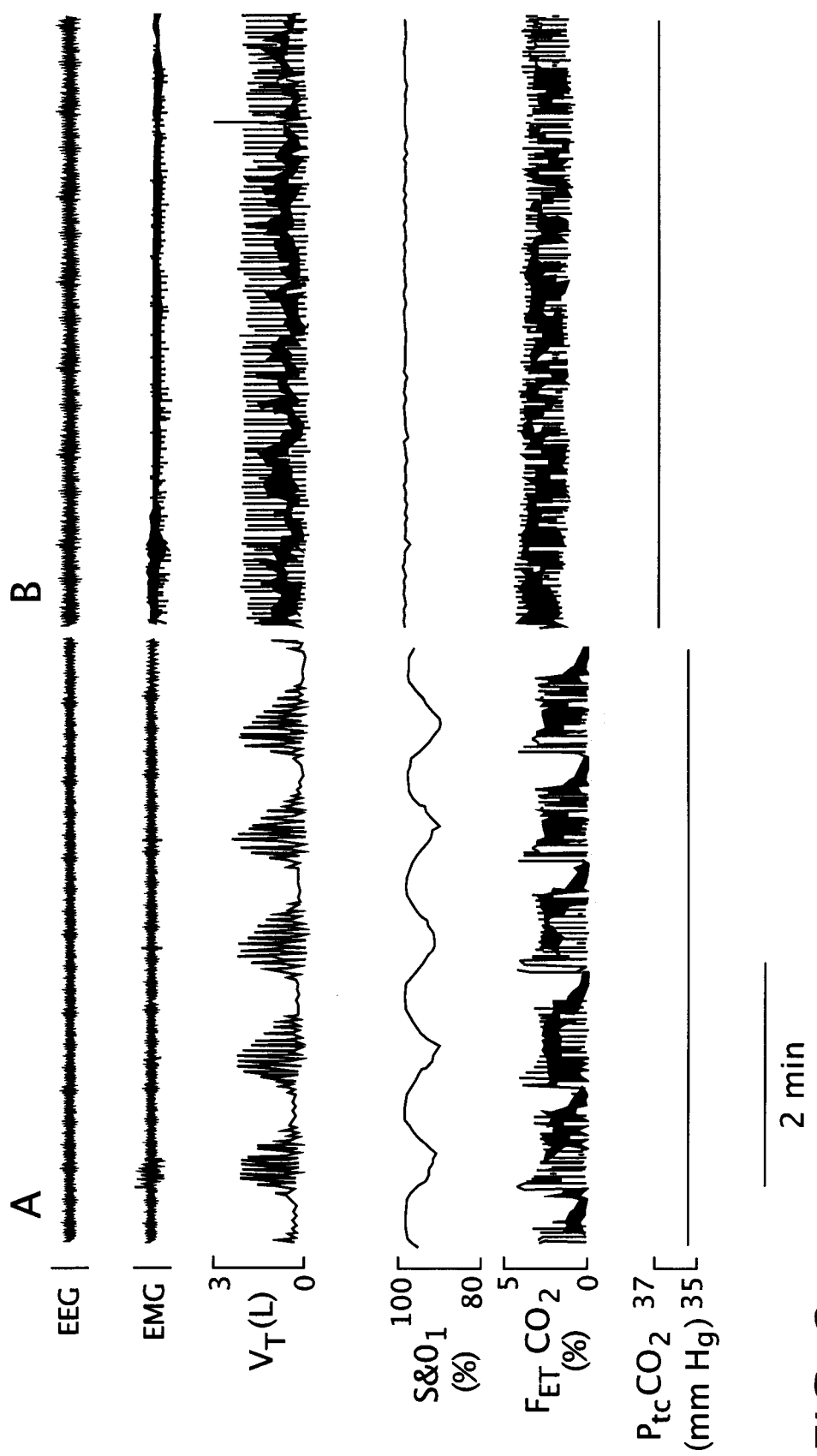
FIG. 2 shows the effect of increasing the fraction of inspired carbon dioxide on a patient exhibiting Cheyne-Stokes respiration.
Figure 8:
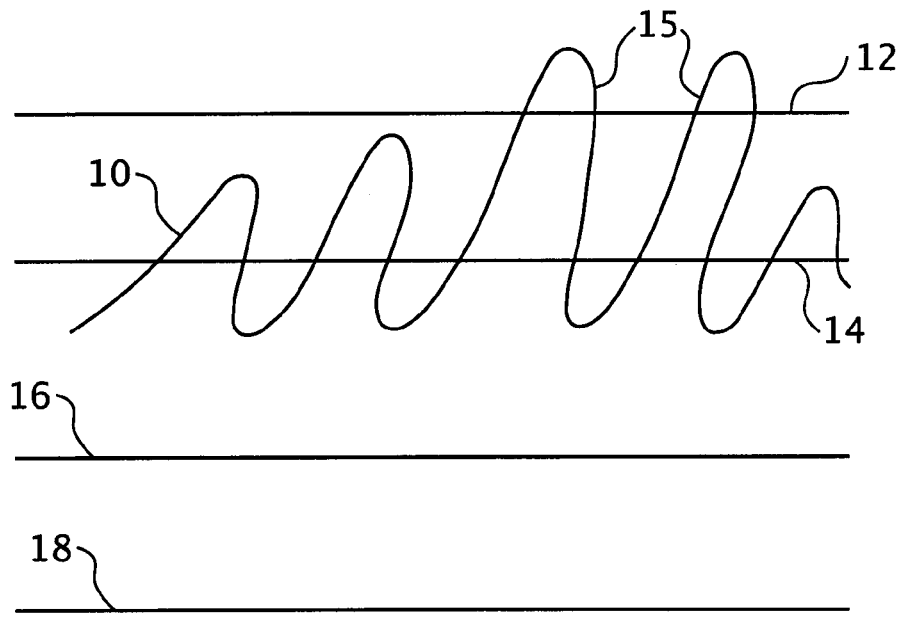
FIG. 8 is a graphical representation of a state of high respiratory drive in accordance with an embodiment of the present invention.

If, as shown in FIG. 8, the patient's indicating characteristic 10 exceeds the upper threshold 12, the controller 64 determines that the patient is in a state of high respiratory drive. As shown in FIG. 8, the peak flow exceeds the upper threshold 12 for peak flow at peaks 15. During this state, therapy to reduce plant gain is implemented, which involves clamping the end tidal $CO_2$ by increasing the $FiCO_2$ using a method described above, such as maintaining dynamic dead space, using a reservoir of trapped $CO_2$ or otherwise implementing rebreathing. By maintaining adequate alveolar $CO_2$, the central apnea or hypopnea that often follows periods of hyperpneas may be attenuated (see the characteristic apneas 38 following hyperpneas 36 in a typical CSR cycle as in FIG. 1).

Although EPAP 18 is shown in FIG. 8 as remaining constant during the high state of ventilation, the present invention also contemplates reducing EPAP 18 during the exhaled breath in order to improve the ability of the circuit to recapture exhaled $CO_2$ in certain rebreathing techniques described above. EPAP 18 may be reduced by a predetermined constant level, according to a predetermined or adaptive waveform, adaptively based on patient history, impulsively, or by any combination of the preceding.

Another example of an apparatus to increase rebreathing, with respect to FIG. 3, is to actively control the exhaust valve 57 such that exhaled gas travels back into the conduit 56. The controller 64 may be operatively linked through link 65 to control the degree of opening of the valve 57 in order to prevent the escape of exhaled gas, thereby increasing the fraction of inspired $CO_2$ in subsequent breaths. A further embodiment may utilize a $CO_2$ reservoir (not shown) attached to the system in proximity to the patient interface 58 to capture exhaled gas and to reinsert the gas into the patient's airway. The reservoir may communicate with the patient interface 58 or conduit 56 through a valve that may be actively controlled by the controller 64.

Having thus described the three respiratory states and the interventions and therapies implemented in each, the disclosure will now turn to the determination of the upper and lower threshold values and the establishment of a dynamic window of normal respiration, i.e., the range between the upper and lower threshold values. It should be understood that the system according to the present invention may be implemented to provide autotitration therapy during any or all respiratory states. Autotitration refers to a minimum level of positive airway pressure supplied to maintain a patient's upper airway so as to prevent obstruction related occurrences such as obstructive sleep apnea, snoring, hypopnea, etc.

To determine a dynamic upper threshold (DUT), the system is initially set to a default or initial value. A default value may be based on prior patient history or may be selected by the clinician. Alternatively, an initial value may be obtained based on a measured parameter, for example, mean peak airflow over a period of time or mean tidal volume over time. Two separate algorithms run in parallel to determine the DUT—one algorithm acts to decrease the DUT and the other acts to increase the DUT. Each will be addressed in turn.

The DUT will be decreased if the system is not responding to unstable breathing. This algorithm calculates a change (e.g., slope of a fitted line) in the mean of a respiratory measure or indicating characteristic (e.g., peak flow, tidal volume, etc.) and, if the change exceeds a predetermined value, decreases the DUT by an amount proportional to that change. If breathing is stable, then there will be little or no changes in the mean respiratory measure over time, so no changes are necessary to the DUT. If breathing is unstable, then there will be changes in the mean respiratory measures over time, indicating a need to decrease the DUT to make the system more sensitive in detecting a high respiratory drive state.

Figure 9:
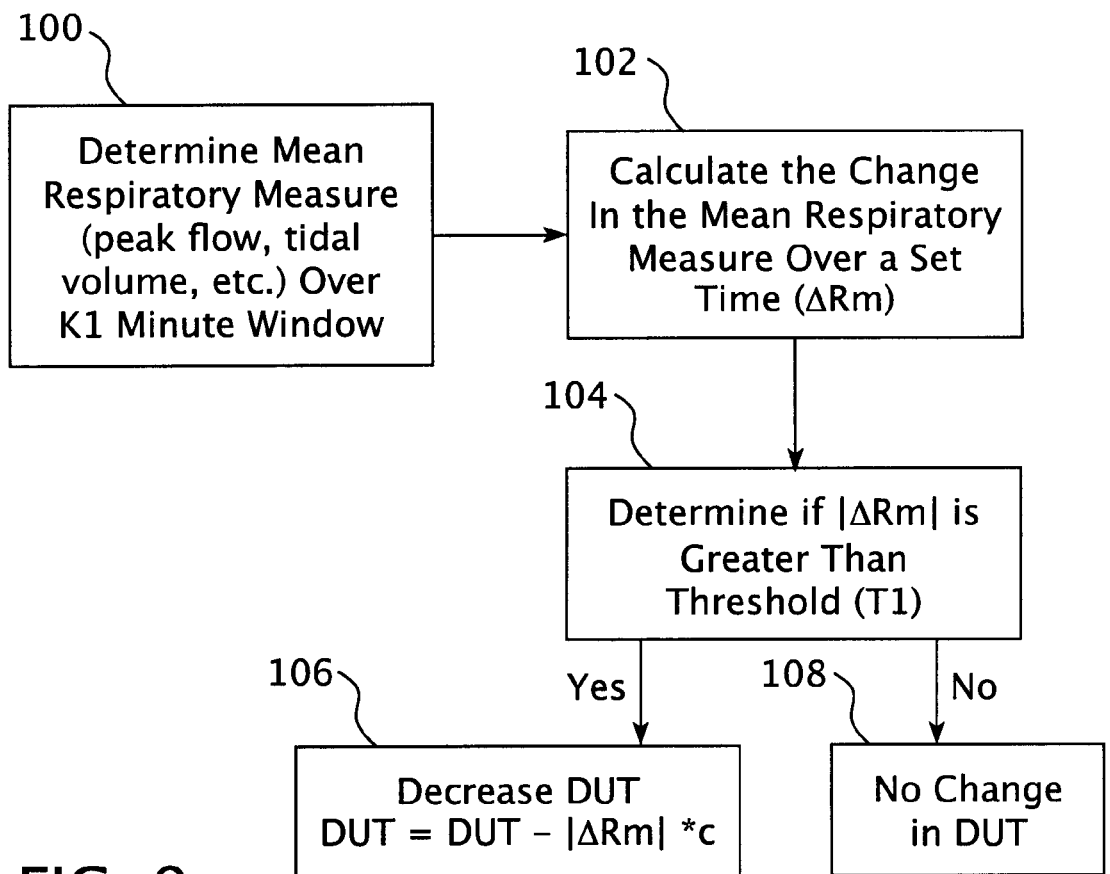
FIG. 9 is a schematic flow diagram of an algorithm for decreasing a dynamic upper threshold in accordance with an embodiment of the present invention.

With reference to FIG. 9, the algorithm to decrease the DUT is schematically illustrated. In step 100, a mean respiratory measure, such as peak flow, tidal volume, or another measure, is determined over a period of time, K1. In step 102, the change in the mean respiratory measure is determined over a period of time to obtain $\Delta Rm$. In step 104, the controller determines whether the absolute value of $\Delta Rm$ ($|\Delta Rm|$) is greater than a predetermined threshold value (T1), which can be preprogrammed by a user, such as a clinician.

If the absolute value of the change in respiratory measure $|\Delta Rm|$ exceeds the threshold value T1, then the controller decreases DUT in step 106 by a quantity proportional to $|\Delta Rm|$. The value "c" in step 106 is a decreasing factor and can be programmed by a user. The value of c may be such that the DUT may be incrementally decreased without adverse or abrupt effects on the patient.

If $|\Delta Rm|$ does not exceed the threshold value T1, then no change is made to DUT, as indicated in step 108. This result indicates that the patient's breathing pattern is steady and, therefore, the sensitivity of the system does not need to be increased.

Figure 10:
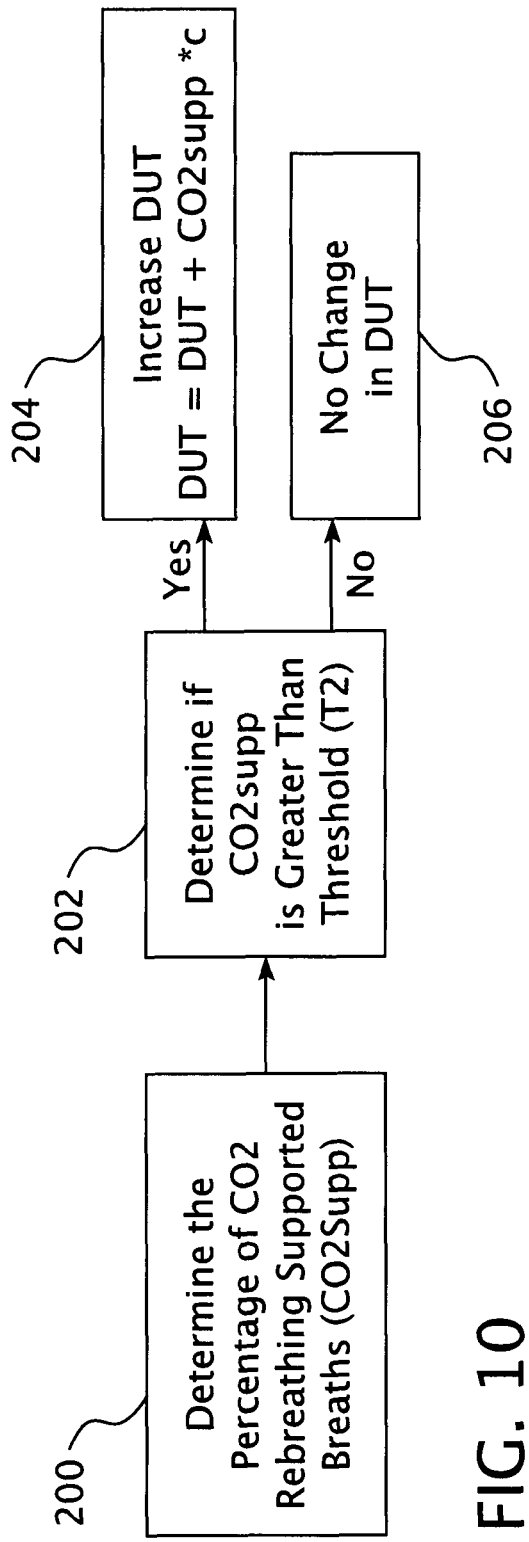
FIG. 10 is a schematic flow diagram of an algorithm for increasing a dynamic upper threshold in accordance with an embodiment of the present invention.

With reference to FIG. 10, there is schematically shown an algorithm for increasing the DUT. In determining whether the DUT should be increased, the question is essentially whether the system is too sensitive. Accordingly, the number of $CO_2$ supported breaths gives a measure of system sensitivity and is therefore the measure used to determine whether the DUT should be increased.

In step 200, the percentage of $CO_2$ rebreathing supported breaths is determined to obtain $CO_{2Supp}$. This percentage is then compared to a preprogrammed threshold value T2 in step 202. If the percentage of $CO_2$ supported breaths $CO_{2Supp}$ exceeds the threshold value T2, then the DUT is increased by an amount proportional to the percentage as indicated in step 204. The factor of increase c may be preprogrammed by a user and may or may not be the same as the factor of decrease used in the algorithm to decrease the DUT, described above.

If the percentage of $CO_2$ supported breaths $CO_{2Supp}$ is less than the threshold value T2, then no change is made to the DUT, as indicated in step 206. This result indicates that the system is not overactive in intervening at the high respiratory drive state and, accordingly, the DUT need not be increased.

The determination of the dynamic lower threshold (DLT) is made in a similar manner to that utilized in the '151 patent and the '520 application, both of which methods are incorporated by reference. Summarily, a mean respiratory measure or indicating characteristic (e.g., peak airflow, tidal volume, etc.) is obtained over a moving time period, such as two minutes, five minutes or some other period of time, and the DLT is dynamically set, or adjusted, at a predetermined factor below the moving mean. Thus, when the instantaneous respiratory measure falls below the adjusted moving average or mean, the controller 64 recognizes a low respiratory drive state and initiates the corresponding intervention(s). Naturally, there is no need for separate algorithms to increase and decrease the DLT as the mean measure over time will inherently increase and decrease.

In accordance with another aspect of the present invention, the state-dependent positive airway pressure system monitors a patient's breathing pattern and identifies trends or changes that predict unstable or clinically undesirable respiratory drive states. If a change in respiratory drive state is predicted, the system may activate or suspend an appropriate therapeutic intervention (e.g., servo-ventilation, increasing alveolar $CO_2$, etc.) to prevent the state from being reached. This represents an advantageous feature in that the system anticipates an undesirable state and acts to remedy the condition before the undesirable state occurs. The system is adaptive in that it "learns" an appropriate therapeutic window based on the efficacy of therapeutic interventions actually performed on the patient. This system may be used in conjunction with a purely state-dependent system as described above or as a standalone system.

Figure 11:
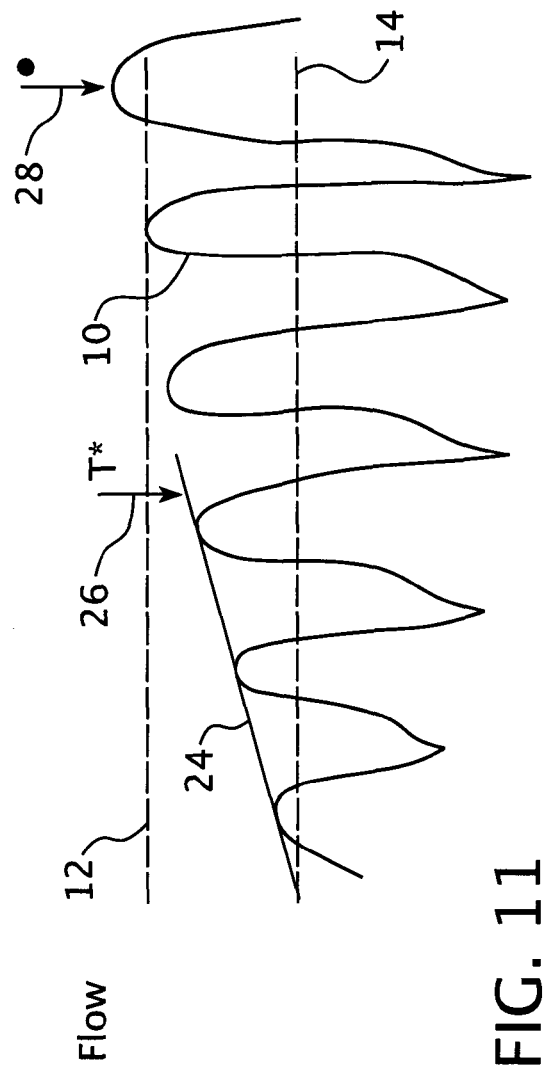
FIG. 11 is a graphical representation of a trend-based prediction method for predicting a high respiratory state when the respiratory measure is peak flow, in accordance with an embodiment of the present invention.

FIG. 11 shows the prediction of a high respiratory state based on a trend of increasing peak flow. As shown, the first three peaks of the flow 10 are within the normal respiratory window (i.e., the peaks are lower than the upper threshold 12 and higher than the lower threshold 14) but are tending toward exceeding the upper threshold 12. In the process by which trends are predicted and state changes are anticipated, the slope 24 of the respiratory measure (here, peak flow) is first determined. If the slope 24 exceeds a predetermined maximum limit, then the controller 64 activates or suspends an appropriate intervention at point 26, such as $CO_2$ rebreathing or dynamic dead space, as discussed above with respect to actual state changes. With this early intervention, the predicted change in respiratory state may be reduced or prevented. Point 28 represents the point at which the system would have activated (or suspended) an intervention therapy without the use of trend prediction. Thus, trend predicting normalizes a patient's breathing pattern much earlier than strict state-dependency and without having to wait until an undesirable state of ventilation occurs.

Figure 12:
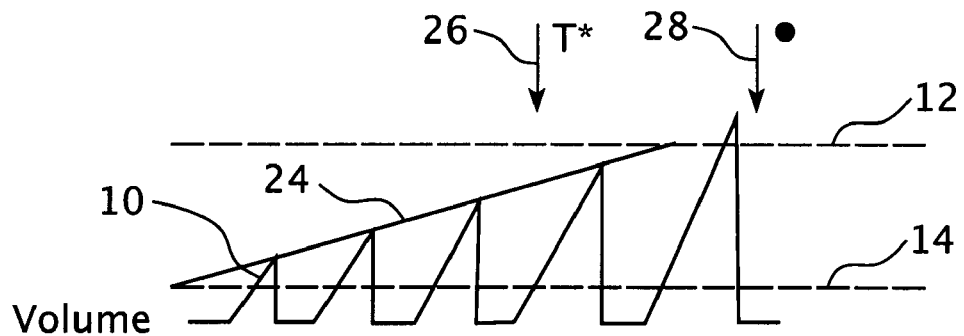
FIG. 12 is a graphical representation of a trend-based prediction method for predicting a high respiratory state when the respiratory measure is tidal volume, in accordance with an embodiment of the present invention.

FIG. 12 shows a high respiratory drive trend, similar to FIG. 11, except that the respiratory measure 10 in this case is tidal volume. As before, the trend is predicted after three respiratory cycles and the slope 24 is determined to exceed a predetermined limit. An intervention therapy is either activated or suspended, whichever is appropriate, at point 26 before an actual change in state occurs and the undesirable effects of a state change are reduced or eliminated altogether.

Figure 13:
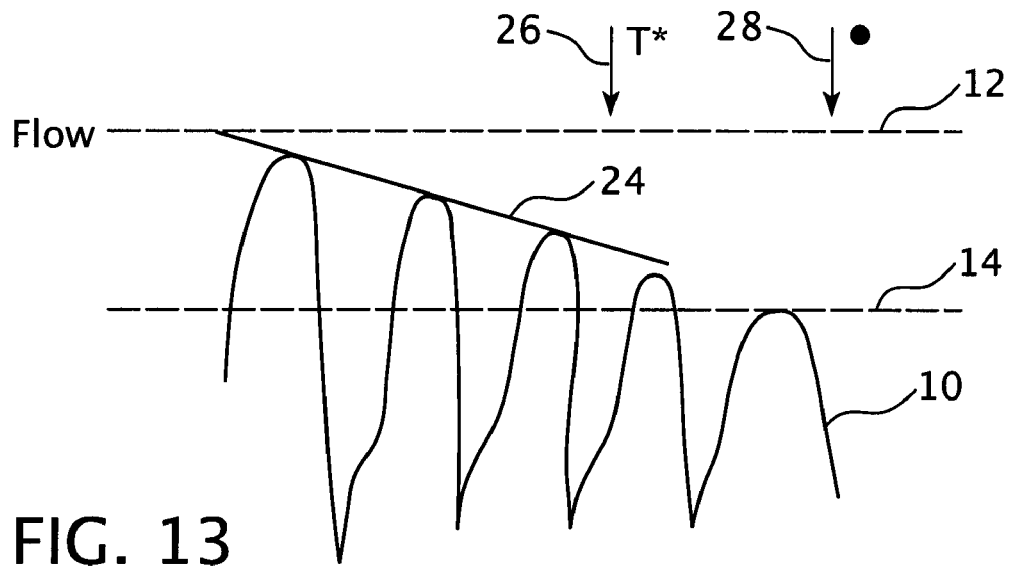
FIG. 13 is a graphical representation of a trend-based prediction method for predicting a low respiratory state when the respiratory measure is peak flow, in accordance with an embodiment of the present invention.
Figure 14:
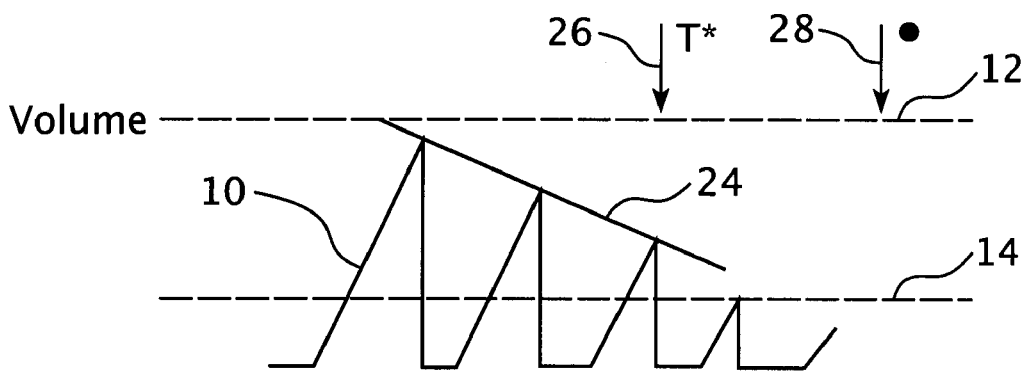
FIG. 14 is a graphical representation of a trend-based prediction method for predicting a low respiratory state when the respiratory measure is tidal volume, in accordance with an embodiment of the present invention.

FIGS. 13 and 14 show the prediction of a low respiratory state when the respiratory measure is peak flow and tidal volume, respectively. The trend is predicted, similar to the prediction of a high respiratory state, based on the slope 24 of three consecutive respiratory cycles. If the slope exceeds a predetermined limit, then an appropriate intervention therapy is activated or suspended accordingly. One of skill in the art would appreciate that a number of respiratory cycles other than three may be used to predict trends, as determined to be appropriate.

Figure 15:
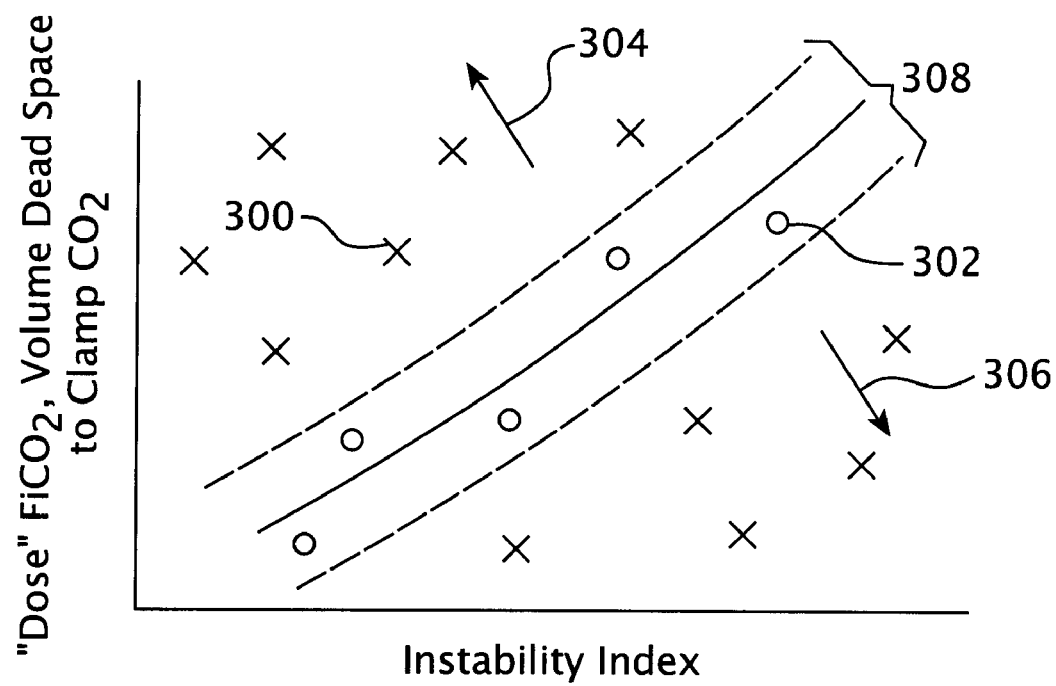
FIG. 15. is a graphical representation of a statistical analysis method for determining an ideal therapeutic window in accordance with an embodiment of the present invention.

The system according to the present invention may further be made to be adaptable to a patient's present condition and to determine an ideal therapeutic window. A therapeutic window refers to the effective range of a $CO_2$ or $O_2$ "dose" during an intervention in order to stabilize respiration. FIG. 15 shows a graph of a number of samples taken from a patient that may be used by the system to determine the ideal therapeutic window. The vertical axis measures the dose of $CO_2$ administered to clamp $CO_2$ during high respiratory drive. The dose of $CO_2$ can also be determined by the volume of dead space. The instability index, measured along the horizontal axis, is a measure of the severity or proportion of unstable breathing due to changes in respiratory drive, and can be derived from parameters such as a) a ratio of the minimum and maximum of a measure such as peak flow or tidal volume, b) the slope of a line fitted to a moving window mean (or median) measure such as peak flow or tidal volume, or c) a measure or predictor of loop gain of the respiratory control system.

The therapeutic window 308 in FIG. 15 represents an appropriate range of doses of fraction of inspired $CO_2$ or volume of dead space used in a particular therapy. Data point 300 represents an occurrence of an unstable event while data point 302 represents the occurrence of a stable event. The stable event 302 is deemed to be in an acceptable therapeutic window 308 based on measured instability parameter(s). Doses of $CO_2$ 304 above the therapeutic window 308 cause hyperventilation and doses 306 below the therapeutic window 308 are not sufficient to stabilize breathing. Thus, by storing a number of data samples, even from day to day, and eliminating old data, the system may always be tuned to a patient's current condition and may adapt to and adjust the therapy line based on the measured patient instabilities. That is, when a dose used in an intervention causes an instability as determined by one or more of the measured instability parameters mentioned above, the controller associates that dose as being either above or below the therapeutic window 308 and makes modifications to the therapeutic window 308 accordingly.

As the above method is adaptive, it learns what is effective for individual patients. Adaptive systems require initial conditions, which are programmed into the system, and updated as experience with patient therapy is acquired. The system may be made more robust by utilizing one or several of the many adaptive control and statistical techniques that are well-described in the literature to make the system effectively adapt to the patient, handle outlying and/or poor data, etc.

While this example describes an intervention for predicted or existing hyperventilation, a similar chart and statistical analysis may be utilized for hypoventilation or central apnea. In that case, a graph can be drawn where $CO_2$ and/or servo-ventilation are utilized to treat the predicted or existing condition. Too little $CO_2$ in this case can cause further washout of $CO_2$ from the patient, exacerbating the central apnea. Too much $CO_2$ could trigger entry into hyperventilation.

Additionally, the system may require more than one dimension of data analysis of therapy optimization, such as temporal data, in the number of physiological parameters input to the algorithm. For example, there may be hysteresis in the system, so the sequence of respiratory states leading to the present state would need to be known to apply the correct therapy.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for delivering a flow of breathing gas to an airway of a patient, the system comprising:
a pressurizing flow module that generates a pressurized flow of breathing gas;
a patient circuit coupled to the pressurizing flow module configured to communicate the flow of breathing gas to an airway of a patient;
a sensor adapted to monitor a characteristic of a breathing pattern of the patient; and
a controller that communicates with the sensor and is configured to identify a state of respiration of the patient based on information received from the sensor, and to effectuate patient treatment based on the state of respiration of the patient,
wherein the controller is further configured such that (i) the state of respiration is identified as a high respiratory drive state responsive to the monitored characteristic exceeding an upper threshold value, (ii) the state of respiration is identified as a normal ventilation state responsive to the monitored characteristic being between the upper threshold value and a lower threshold value, and (iii) the state of respiration is identified as a low respiratory drive state responsive to the monitored characteristic being below the lower threshold value,
wherein the controller is further configured such that effectuating patient treatment based on the state of respiration of the patient treatment includes increasing a fraction of inspired carbon dioxide responsive to the state of respiration being the high respiratory drive state and providing servo-ventilation responsive to the state of respiration being the low respiratory drive state, and
wherein the controller is further configured such that the upper threshold value is decreased responsive to a change in a mean value of the monitored characteristic exceeding a predetermined limit, such that the upper threshold value is increased responsive to a frequency of carbon dioxide supported breaths supplied to the patient exceeding a predetermined frequency, and such that the lower threshold value is changed based on the monitored characteristic.

2. The system of claim 1, wherein the controller is configured to increase the fraction of inspired carbon dioxide in addition to providing servo-ventilation when the state of respiration is the low respiratory drive state.

3. The system of claim 1, wherein the controller is configured to increase the fraction of inspired carbon dioxide by carrying out one or more of effectuating rebreathing, providing a supplemental source of carbon dioxide, or providing carbon dioxide from a reservoir adapted to capture exhaled breathing gas.

4. The system of claim 1, wherein the pressurizing flow module comprises one or more of a blower or a valve.

5. The system of claim 1, wherein the upper threshold value and lower threshold value can converge equal to the same single value.

6. The system of claim 1, wherein the monitored characteristic is peak flow of the patient or a tidal volume of the patient.

7. The system of claim 1, wherein the controller provides servo-ventilation by supplying an increasing ratio of inspiratory pressure to expiratory pressure.

8. A system for delivering a flow of breathing gas to an airway of a patient, the system comprising:
a pressurizing flow module that generates a flow of breathing gas;
a patient circuit coupled to the pressurizing flow module configured to communicate the flow of breathing gas to an airway of a patient;
a sensor for monitoring a characteristic of a breathing pattern of the patient;
a carbon dioxide supplement system associated with said patient circuit; and
a controller operatively connected with said pressurizing flow module and carbon dioxide supplement system, said controller communicating with said sensor and configured to effectuate patient treatment based on a state of respiration of the patient,
wherein the controller is further configured such that (i) the state of respiration is identified as a high respiratory drive state responsive to the monitored characteristic exceeding an upper threshold value, (ii) the state of respiration is identified as a normal ventilation state when the monitored characteristic is between the upper threshold value and a lower threshold value, and (iii) the state of respiration is identified as a low respiratory drive state responsive to the monitored characteristic being below the lower threshold value,
wherein the controller is further configured such that the patient treatment includes increasing an amount of carbon dioxide in said patient circuit for inspiration by the patient responsive to the state of respiration being the high respiratory drive state and controlling said gas flow generator module to increase a ratio of inspiratory pressure to expiratory pressure provided to the airway of the patient responsive to the state of respiration being the low respiratory drive, and
wherein the controller is further configured such that the upper threshold value is decreased when a change in a mean value of the monitored characteristic exceeds a predetermined limit and the upper threshold value is increased when a frequency of carbon dioxide supported breaths supplied to the patient exceeds a predetermined frequency, and wherein the lower threshold value is changed based on the monitored characteristic.

9. The system of claim 8, wherein the pressurizing flow module comprises one or more or a blower or a valve.

10. The system of claim 8, wherein the carbon dioxide supplement system comprises one or more of:
a valve that directs expired carbon dioxide back to the patient for rebreathing;
an external carbon dioxide source communicating with the patient circuit; Or
a carbon dioxide reservoir for capturing exhaled breathing gas.

11. The system of claim 8, wherein the upper threshold value and lower threshold value can converge to equal to the same single value.

12. The system of claim 8, wherein the monitored characteristic is peak flow of the patient or a tidal volume of the patient.

13. The system of claim 8, wherein the system provides an increasing ratio of inspiratory pressure to expiratory pressure responsive to the state of respiration being the low respiratory drive state.

14. A method for determining states of ventilation of a patient undergoing respiratory therapy, the method comprising:

delivering a flow of gas to the airway of the patient from a source of breathing gas via a patient circuit;

monitoring a characteristic of a breathing pattern of a patient;

establishing a lower threshold value for the monitored characteristic based on a mean value of the monitored characteristic over a period of time; and establishing an upper threshold value for the monitored characteristic based on an initial value for the monitored characteristic, wherein a state of respiration is based on one or more of the upper threshold value or the lower threshold value, the state of respiration being identified as a high respiratory drive state responsive to the monitored characteristic exceeding an upper threshold value, the state of respiration being identified as a normal ventilation state responsive to the monitored characteristic being between the upper threshold value and a lower threshold value, and the state of respiration being identified as a low respiratory drive state responsive to the monitored characteristic being below the lower threshold value; and adapting the upper threshold value such that the upper threshold value is decreased responsive to a change in a mean value of the monitored characteristic exceeding a predetermined limit and the upper threshold value is increased responsive to a frequency of carbon dioxide supported breaths supplied to the patient exceeding a predetermined frequency.

15. The method of claim 14, wherein the carbon dioxide supported breaths are supplied to the patient by way of carbon dioxide rebreathing.

16. The method of claim 14, wherein the lower threshold value is obtained by reducing the mean value of the monitored characteristic over time by a predetermined factor.

17. A method for treating a patient, the method comprising:

delivering a flow of gas to the airway of the patient from a source of breathing gas via a patient circuit;

monitoring a characteristic of the breathing pattern of the patient;

predicting a state respiration of the patient, the state of respiration being identified as a high respiratory drive state responsive to the monitored characteristic exceeding an upper threshold value, the state of respiration being identified as a normal ventilation state responsive to the monitored characteristic being between the upper threshold value and a lower threshold value, and the state of respiration being identified as a low respiratory drive state responsive to the monitored characteristic being below the lower threshold value;

adapting the upper threshold value such that the upper threshold value is decreased responsive to a change in a mean value of the monitored characteristic exceeding a predetermined limit and the upper threshold value is increased responsive to a frequency of carbon dioxide supported breaths supplied to the patient exceeds a predetermined frequency;

adapting the lower threshold value such that the lower threshold value is changed based on the monitored characteristic; and applying an appropriate treatment to the patient based on the predicted state of respiration, the appropriate treatment including increasing a fraction of inspired carbon dioxide responsive to the state of respiration being the high respiratory drive state and providing servo-ventilation responsive to the state of respiration being the low respiratory drive state.

18. The method of claim 17, wherein the monitored characteristic is peak flow or tidal volume.

19. The method of claim 17, wherein the mean value of the monitored characteristic is determined over a predetermined number of breathing cycles.

20. A method of delivering pressurized breathing gas to an airway of a patient, the method comprising:

delivering a flow of gas to the airway of the patient from a source of breathing gas via a patient circuit;

monitoring a characteristic of the breathing pattern of the patient;

determining a state of respiration of the patient, wherein the state of respiration is identified as a high respiratory drive state responsive to the monitored characteristic exceeding an upper threshold value, the state of respiration is identified as a normal ventilation state responsive to the monitored characteristic being between the upper threshold value and a lower threshold value, and the state of respiration is identified as a low respiratory drive state responsive to the monitored characteristic being below the lower threshold value;

decreasing the upper threshold value responsive to a change in a mean value of the monitored characteristic exceeding a predetermined limit;

increasing the upper threshold value responsive to a frequency of carbon dioxide supported breaths supplied to the patient exceeding a predetermined frequency;

changing the lower threshold value based on the monitored characteristic;

increasing the fraction of inspired carbon dioxide responsive to the state of respiration being the high respiratory drive state; and providing servo-ventilation responsive to the state of respiration being the low respiratory drive state.

* * * * *